US010974232B2

United States Patent
Kumagai et al.

(10) Patent No.: US 10,974,232 B2
(45) Date of Patent: Apr. 13, 2021

(54) CATALYST, METHOD FOR FORMING AMIDE BOND, AND METHOD FOR PRODUCING AMIDE COMPOUND

(71) Applicant: Microbial Chemistry Research Foundation, Tokyo (JP)

(72) Inventors: Naoya Kumagai, Tokyo (JP); Christopher Roderick Opie, Tokyo (JP); Hidetoshi Noda, Tokyo (JP); Masakatsu Shibasaki, Tokyo (JP)

(73) Assignee: Microbial Chemistry Research Foundation, Tokyo (JP)

( * ) Notice: Subject to any disclaimer, the term of this patent is extended or adjusted under 35 U.S.C. 154(b) by 0 days.

(21) Appl. No.: 16/639,248

(22) PCT Filed: Aug. 14, 2018

(86) PCT No.: PCT/JP2018/030267
§ 371 (c)(1),
(2) Date: Feb. 14, 2020

(87) PCT Pub. No.: WO2019/035453
PCT Pub. Date: Feb. 21, 2019

(65) Prior Publication Data
US 2020/0206724 A1 Jul. 2, 2020

(30) Foreign Application Priority Data

Aug. 16, 2017 (JP) .............................. JP2017-156990

(51) Int. Cl.
*B01J 31/02* (2006.01)
*C07C 231/02* (2006.01)
*C07F 5/05* (2006.01)

(52) U.S. Cl.
CPC ......... *B01J 31/0272* (2013.01); *C07C 231/02* (2013.01); *C07F 5/05* (2013.01)

(58) Field of Classification Search
CPC ............................... C07F 5/05; B01J 31/0272
See application file for complete search history.

(56) References Cited

U.S. PATENT DOCUMENTS

| 6,121,471 A | 9/2000 | Scott |
| 2010/0197960 A1 | 8/2010 | Hall et al. |
| 2014/0018576 A1 | 1/2014 | Cantat et al. |

FOREIGN PATENT DOCUMENTS

| JP | 2002-511386 | 4/2002 |
| JP | 2010-538021 | 12/2010 |
| JP | 2014-517815 | 7/2014 |

OTHER PUBLICATIONS

Roughley, et al., "The Medicinal Chemist's Toolbox: An Analysis of Reactions Used in the Pursuit of Drug Candidates", Journal of Medicinal Chemistry, 2011, vol. 54, pp. 3451-3479.
Constable, et al., "Key green chemistry research areas—a perspective from pharmaceutical manufacturers", Green Chemistry, 2007, vol. 9, Issue 5, pp. 411-420.
Lundberg, et al., "Catalytic amide formation from non-activated carboxylic acids and amines", Chem. Soc. Rev., 2014, vol. 43, pp. 2714-2742.
Gernigon, et al. "Direct Amidation of Carboxylic Acids Catalyzed by ortho-Iodo Arylboronic Acids: Catalyst Optimization, Scope, and Preliminary Mechanistic Study Supporting a Peculiar Halogen Acceleration Effect", J. Org. Chem., 2012, vol. 77, pp. 8386-8400.
Noda, et al., "Unique physicochemical and catalytic properties dictated by the B3NO2 ring system", Nature Chemistry, Jan. 30, 2017, pp. 1-7, DOI: 10.1038/nchem. 2708.
Noda, et al., "A Novel Multiboron Catalyst for Direct Amidation" Abstracts of 14th Organic Chemistry Symposium leading the Next Generation, May 19, 2016, pp. 34-35.
International Search Report dated Nov. 13, 2018 issued in corresponding International Patent Application No. PCT/JP2018/030267.
Written Opinion of the International Search Authority dated Nov. 13, 2018 issued in corresponding International Patent Application No. PCT/JP2018/030267.

*Primary Examiner* — Emily A Bernhardt
(74) *Attorney, Agent, or Firm* — Carmody Torrance Sandak & Hennessey LLP

(57) ABSTRACT

A catalyst represented by General Formula (1) below:

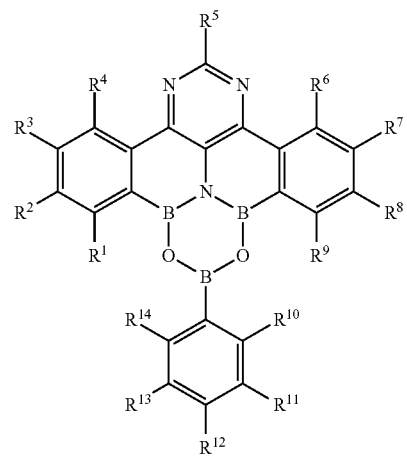

General Formula (1)

where in the General Formula (1), $R^1$ to $R^{14}$ each independently represent a hydrogen atom or a substituent.

4 Claims, No Drawings

CATALYST, METHOD FOR FORMING AMIDE BOND, AND METHOD FOR PRODUCING AMIDE COMPOUND

TECHNICAL FIELD

The present invention relates to a novel catalyst, a method for forming an amide bond using the catalyst, and a method for producing an amide compound using the same.

BACKGROUND ART

An amide bond is a basic constitutional unit of synthesized polymers such as biopolymers (e.g., proteins) and nylons and is contained in 25% of synthesized pharmaceuticals. Therefore, the amide bond forming reaction has considerably high industrial usability (see NPL 1).

The amide bond forming reaction is generally performed using a stoichiometric activator. Use of such an activator generates a desired amide, while there is a problem that a large amount of waste products are formed as a by-product.

Then, the working group, which consists of a plurality of pharmaceutical companies that belong to American Chemical Society Green Chemistry Institute, selects "the amide bond forming reaction that generates less waste products" as reaction that should be the most desirably developed in 2006 (see NPL 2).

In recent years, catalytic amide bond forming reaction has been considered and has been proposed (see NPL 3).

For example, reaction using an enzymatic catalyst has been proposed. In this reaction, however, there is a problem that an applicable range of a substrate with respect to the enzyme is limited.

For example, reaction using a metallic catalyst has been proposed. In this reaction, however, there is a problem that the reaction requires a high temperature of about 150° C.

For example, reaction using boric acid, aromatic boronic acid, or aromatic borinic acid as a catalyst has been proposed (see NPL 4). In this method, however, about 10 mol % of the catalyst is used relative to the substrate and the yield is about 50% to about 60%. In particular, this method is problematic in terms of the following points. Specifically, an applicable range of the substrate is limited. More specifically, this method is not suitable for reaction of a substrate having a sterically bulky group.

The present inventors have proposed a catalyst represented by the following Structural Formula as a catalyst that can be used for amide bond forming reaction, does not require a high temperature in reaction to be used, and is applicable in a wide range of substrates (see NPL 5).

This catalyst is a catalyst that can be used for amide bond forming reaction, does not require a high temperature in reaction to be used, and is applicable in a wide range of substrates. However, this catalyst requires an expensive modified boron reagent in synthesizing the catalyst and requires multistep synthesis. Therefore, there is room for improvement.

In addition, it is difficult or impossible to collect and reutilize this catalyst after amide bond forming reaction.

Therefore, there is a demand for such a catalyst that can be used for amide bond forming reaction, does not require a high temperature in reaction to be used, and is applicable in a wide range of substrates, and that can be synthesized with less steps, can be produced at a low cost, and can be collected and reutilized.

CITATION LIST

Non-Patent Literatures

NPL 1: J. Med. Chem., 2011, 54, 3451.
NPL 2: Green Chem., 2007, 5, 411.
NPL 3: Chem. Soc. Rev., 2014, 43, 2714.
NPL 4: J. Org. Chem., 2012, 77, 8386.
NPL 5: Nature Chemistry 9, 571-577 (2017)

SUMMARY OF INVENTION

Technical Problem

An object of the present invention is to solve the conventionally existing problems and to achieve the following objects. That is, the objects of the present invention are to provide such a catalyst that can be used for amide bond forming reaction, does not require a high temperature in reaction to be used, and is applicable in a wide range of substrates, and that can be synthesized with less steps, can be produced at a low cost, and can be collected and reutilized, and to provide a method for forming an amide bond using the catalyst and a method for producing an amide compound using the catalyst.

Solution to Problem

Means for solving the above problems are as follows. That is,

A catalyst of the present invention is represented by General Formula (1) below.

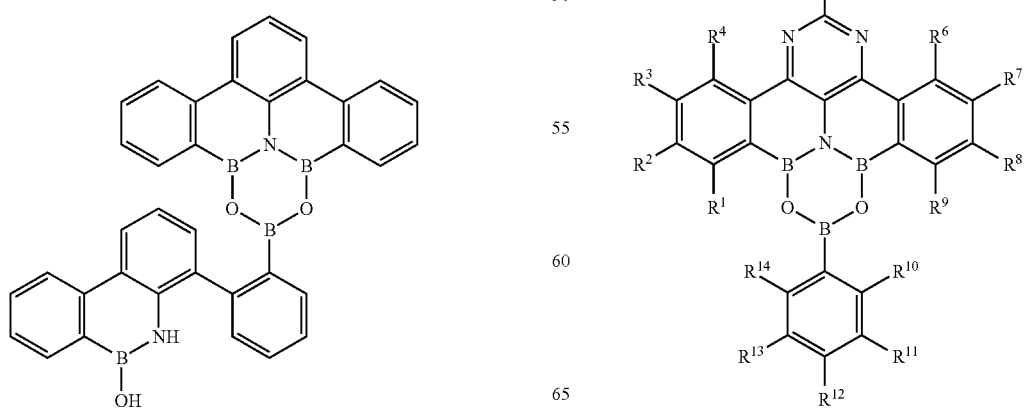

General Formula (1)

In the General Formula (1), $R^1$ to $R^{14}$ each independently represent a hydrogen atom or a substituent.

A method of the present invention for forming an amide bond includes reacting a carboxyl group of a carboxylic acid compound with an amino group of an amine compound in the presence of the catalyst of the present invention to form the amide bond.

A method of the present invention for producing an amide compound includes reacting a carboxylic acid compound with an amine compound in the presence of the catalyst of the present invention to obtain the amide compound.

Advantageous Effects of Invention

According to the present invention, it is possible to solve the conventionally existing problems, to achieve the aforementioned objects, to provide such a catalyst that can be used for amide bond forming reaction, does not require a high temperature in reaction to be used, and is applicable in a wide range of substrates, and that can be synthesized with less steps, can be produced at a low cost, and can be collected and reutilized, and to provide a method for forming an amide bond using the catalyst and a method for producing an amide compound using the catalyst.

DESCRIPTION OF EMBODIMENTS

Catalyst

A catalyst of the present invention is represented by General Formula (1) below.

General Formula (1)

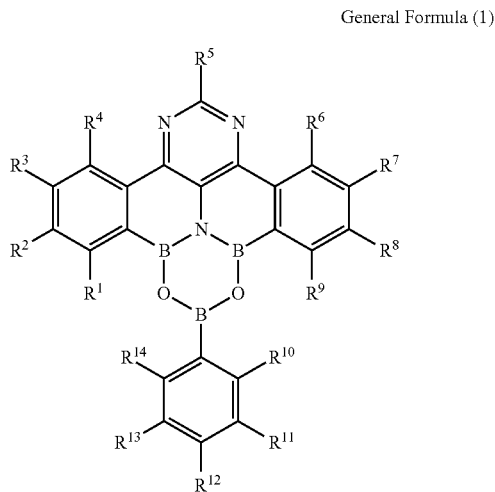

In the General Formula (1), $R^1$ to $R^{14}$ each independently represent a hydrogen atom or a substituent.

Substituent

The substituent is not particularly limited and may be appropriately selected depending on the intended purpose. Examples thereof include electron donative groups and electron attractive groups.

The catalyst functions as a catalyst in the amide bond forming reaction even when an electron donative group or an electron attractive group is included in $R^1$ to $R^{14}$ in the General Formula (1).

Electron Donative Group

Examples of the electron donative group include an alkyl group, a hydroxyl group, a mercapto group, an alkyloxy group, an acyloxy group, a sulfonyloxy group, an alkoxycarbonyloxy group, an aryloxycarbonyloxy group, an alkylthio group, an amino group, and a mono- or di-substituted amino group.

The alkyl group is preferably an alkyl group having 1 to 20 carbon atoms, more preferably an alkyl group having 1 to 12 carbon atoms, particularly preferably an alkyl group having 1 to 6 carbon atoms.

Examples of the alkyl group include a methyl group, an ethyl group, a propyl group, an isopropyl group, a butyl group, an isobutyl group, a s-butyl group, a t-butyl group, a hexyl group, a decyl group, a dodecyl group, a tetradecyl group, and a hexadecyl group.

The alkyloxy group is preferably an alkyloxy group having 1 to 20 carbon atoms, more preferably an alkyloxy group having 1 to 12 carbon atoms, particularly preferably an alkyloxy group having 1 to 6 carbon atoms.

Examples of the alkyloxy group include a methoxy group, an ethoxy group, an isopropoxy group, a butoxy group, a t-butoxy group, a hexyloxy group, an octyloxy group, a decyloxy group, a dodecyloxy group, a tetradecyloxy group, and an octadecyloxy group.

The acyloxy group is preferably an acyloxy group having 1 to 20 carbon atoms, more preferably an acyloxy group having 1 to 12 carbon atoms, particularly preferably an acyloxy group having 1 to 6 carbon atoms.

Examples of the acyloxy group include a formyloxy group, an acetyloxy group, a propionyloxy group, and a benzoyloxy group.

Examples of the sulfonyloxy group include a benzenesulfonyloxy group and a p-toluene sulfonyloxy group.

The alkoxycarbonyloxy group is preferably an alkoxycarbonyloxy group having 2 to 21 carbon atoms, more preferably an alkoxycarbonyloxy group having 2 to 13 carbon atoms, particularly preferably an alkoxycarbonyloxy group having 2 to 7 carbon atoms.

Examples of the aryloxycarbonyloxy group include a phenyloxycarbonyloxy group.

The alkylthio group is preferably an alkylthio group having 1 to 20 carbon atoms, more preferably an alkylthio group having 1 to 12 carbon atoms, particularly preferably an alkylthio group having 1 to 6 carbon atoms.

Examples of the mono- or di-substituted amino group include a mono- or di-alkylamino group, an acylamino group, and a sulfonylamino group.

Electron Attractive Group

Examples of the electron attractive group include a halogen atom, a haloalkyl group, an aryl group, a carboxyl group, an alkyloxycarbonyl group, an aryloxycarbonyl group, an aralkyloxycarbonyl group, an acyl group, a cyano group, a nitro group, a sulfo group, and an alkyloxysulfonyl group.

Examples of the halogen atom include a fluorine atom, a chlorine atom, a bromine atom, and an iodine atom.

The haloalkyl group is preferably a haloalkyl group having 1 to 20 carbon atoms, more preferably a haloalkyl group having 1 to 12 carbon atoms, particularly preferably a haloalkyl group having 1 to 6 carbon atoms.

Examples of the haloalkyl group include a fluoromethyl group, a difluoromethyl group, a trifluoromethyl group, a chloromethyl group, a dichloromethyl group, a trichloromethyl group, and a bromomethyl group.

Examples of the aryl group include a phenyl group, a tolyl group, a xylyl group, and a naphthyl group.

The alkyloxycarbonyl group is preferably an alkyloxycarbonyl group having 1 to 20 carbon atoms, more preferably an alkyloxycarbonyl group having 1 to 12 carbon atoms, particularly preferably an alkyloxycarbonyl group having 1 to 6 carbon atoms.

Examples of the alkyloxycarbonyl group include a methoxycarbonyl group, an ethoxycarbonyl group, an isopropoxycarbonyl group, a butoxycarbonyl group, a t-butoxycarbonyl group, and a hexyloxycarbonyl group.

The aryloxycarbonyl group is preferably an aryloxycarbonyl group having 6 to carbon atoms.

Examples of the aryloxycarbonyl group include a phenyloxycarbonyl group and a naphthyloxycarbonyl group.

The aralkyloxycarbonyl group is preferably an aralkyloxycarbonyl group having 7 to 21 carbon atoms.

Examples of the aralkyloxycarbonyl group include a benzyloxycarbonyl group.

The acyl group is preferably an acyl group having 1 to 20 carbon atoms, more preferably an acyl group having 1 to 12 carbon atoms, particularly preferably an acyl group having 1 to 6 carbon atoms.

Examples of the acyl group include aliphatic acyl groups and aromatic acyl groups.

Examples of the acyl group include a formyl group, an acetyl group, a propionyl group, a butyryl group, an isobutyryl group, a valeryl group, a pivaloyl group, a hexanoyl group, a benzoyl group, and a naphthoyl group.

The alkyloxysulfonyl group is preferably an alkyloxysulfonyl group having 1 to 20 carbon atoms, more preferably an alkyloxysulfonyl group having 1 to 12 carbon atoms, particularly preferably an alkyloxysulfonyl group having 1 to 6 carbon atoms.

Examples of the alkyloxysulfonyl group include a methoxysulfonyl group and an ethoxysulfonyl group.

—$R^{10}$ and $R^{14}$—

Moreover, $R^{10}$ and $R^{14}$ may be a group represented by General Formula (2) below as the electron attractive group, or may be a group represented by General Formula (3) below as the electron attractive group.

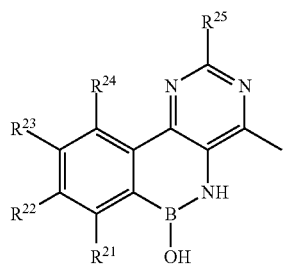

General Formula (2)

In the General Formula (2), $R^{21}$ to $R^{25}$ each independently represent a hydrogen atom or a substituent.

Examples of the substituent include the substituents exemplified in the description of the substituents in the General Formula (1).

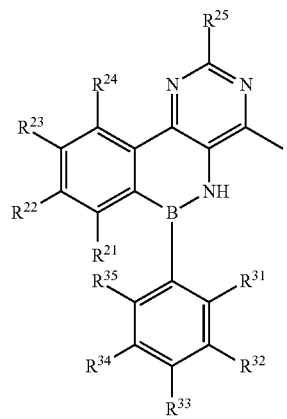

General Formula (3)

In the General Formula (3), $R^{21}$ to $R^{25}$ and $R^{31}$ to $R^{35}$ each independently represent a hydrogen atom or a substituent.

Examples of the substituent include the substituents exemplified in the description of the substituents in the General Formula (1).

For example, $R^{21}$ to $R^{25}$ are the following groups.

$R^{21}$ is the same group as that of $R^1$.

$R^{22}$ is the same group as that of $R^2$.

$R^{23}$ is the same group as that of $R^3$.

$R^{24}$ is the same group as that of $R^4$.

$R^{25}$ is the same group as that of $R^5$.

It is preferable that the catalyst represented by the General Formula (1) be, for example, a catalyst represented by General Formula (1A) below and a catalyst represented by General Formula (1B) below.

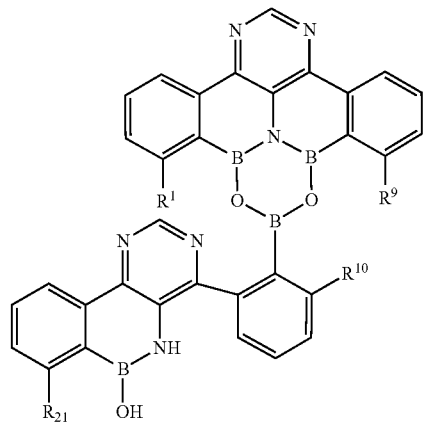

General Formula (1A)

General Formula (1B)

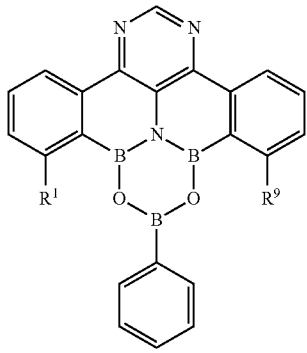

In the General Formula (1A), $R^1$, $R^9$, $R^{10}$, and $R^{21}$ each independently represent a hydrogen atom, an electron donative group, or an electron attractive group. $R^1$, $R^9$, $R^{10}$, and $R^{21}$ are preferably the same substituent.

In the General Formula (1B), $R^1$ and $R^9$ each independently represent a hydrogen atom, an electron donative group, or an electron attractive group.

Examples of the catalyst represented by the General Formula (1) include a catalyst represented by Structural Formula (1A) below and a catalyst represented by Structural Formula (1B). The catalyst of the present invention is not limited to the following Structural Formulas.

Structural Formula (1A)

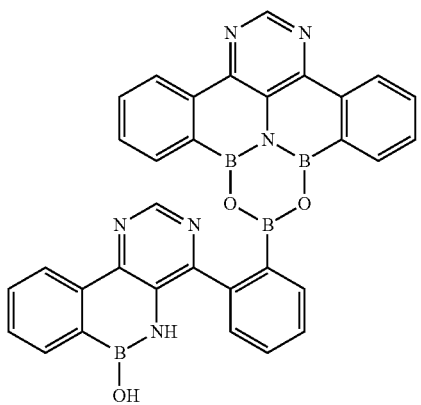

Structural Formula (1B)

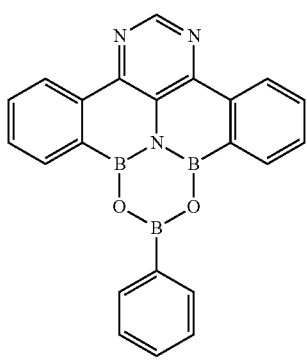

Structural Formula (1C)

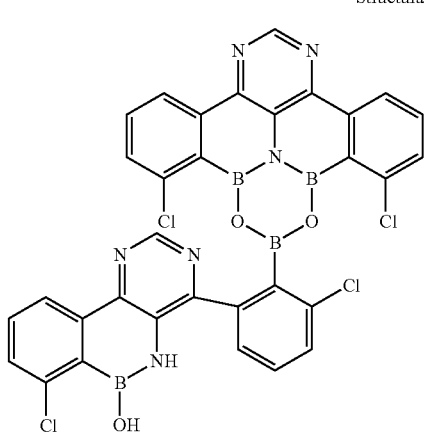

The catalyst of the present invention can be used for amide bond forming reaction, does not require a high temperature in reaction to be used, and is applicable in a wide range of substrates.

In addition, the catalyst of the present invention can be collected and reutilized in amide bond forming reaction. The catalyst that has been reported in Non-Patent Literature [Nature Chemistry 9, 571-577 (2017)] cannot be collected and reutilized. Therefore, it is assumed that inclusion of a pyrimidine ring in the catalyst of the present invention effectively contributes to the aforementioned effect.

Method for Producing Catalyst

A method of the present invention for producing a catalyst is not particularly limited and may be appropriately selected depending on the intended purpose. Examples thereof include methods exemplified in the following reaction schemes. More specific production methods will be described in Examples that will be described hereinafter.

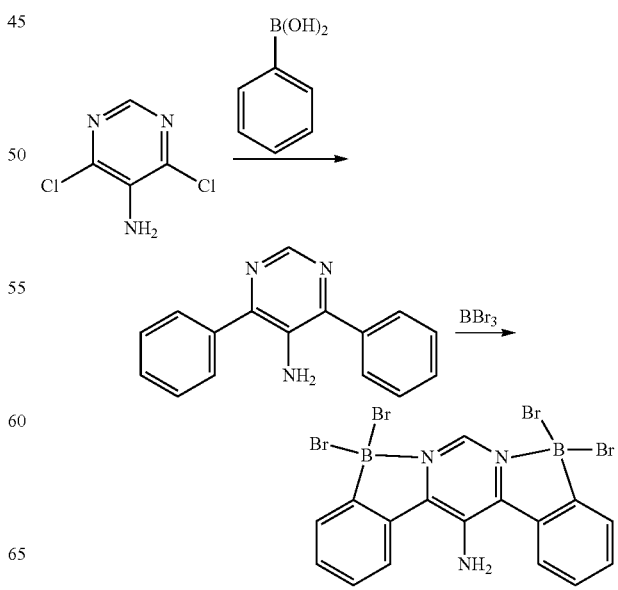

-continued

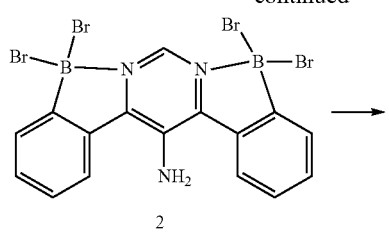

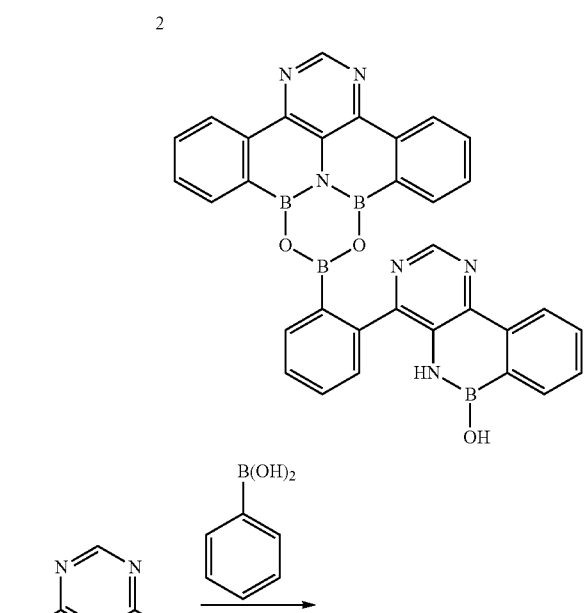

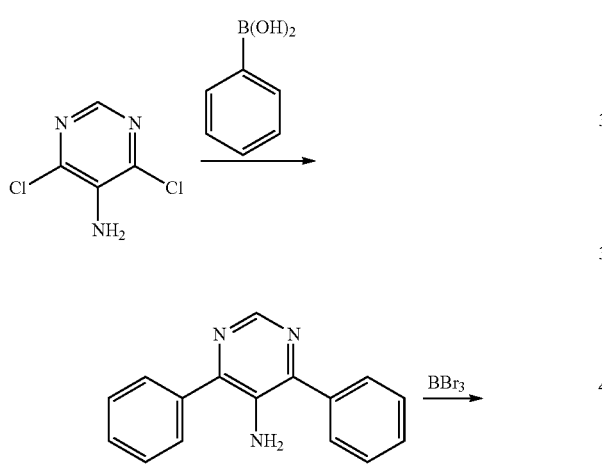

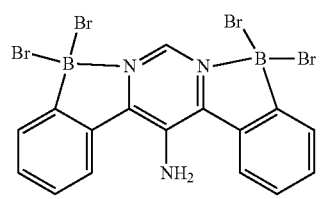

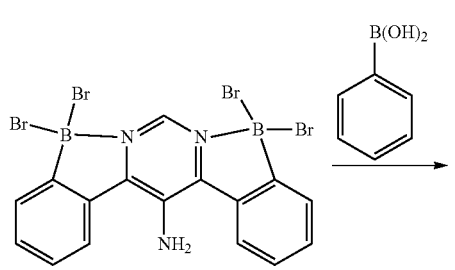

-continued

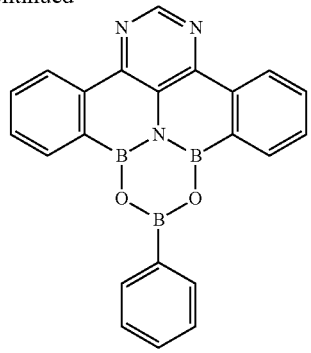

As presented in the aforementioned schemes, the catalyst of the present invention does not use an expensive modified boron reagent that is used when the catalyst of the following Structural Formula is produced in Non-Patent Literature [Nature Chemistry 9, 571-577 (2017)], and can be produced with less steps compared to the catalyst of the following Structural Formula.

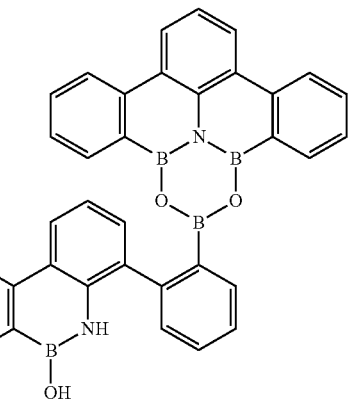

Method for Forming Amine Bond and Method for Producing Amide Compound

In a method of the present invention for forming an amide bond, a carboxyl group of a carboxylic acid compound is reacted with an amino group of an amine compound in the presence of the catalyst of the present invention to form the amide bond.

In a method of the present invention for producing an amide compound, a carboxylic acid compound is reacted with an amine compound in the presence of the catalyst of the present invention to obtain the amide compound.

Carboxylic Acid Compound

In the amide bond forming reaction using a conventional boron catalyst, a sterically bulky carboxylic acid compound cannot be used as a substrate.

Meanwhile, the catalyst of the present invention can be used even when a sterically bulky carboxylic acid compound is used as a substrate of the amide bond forming reaction, which is different from the conventional boron catalysts used in the amide bond forming reaction.

Therefore, in the method for forming the amide bond and the method for producing the amide compound, the carboxylic acid compound is not particularly limited and may be appropriately selected depending on the intended purpose, so long as it is a compound having a carboxyl group.

The carboxylic acid compound may be a monocarboxylic acid compound, or may be a polycarboxylic acid compound. The monocarboxylic acid compound is a compound having one carboxyl group in a molecule thereof. The polycarboxylic acid compound is a compound having two or more carboxyl groups in a molecule thereof.

When the carboxylic acid compound is the polycarboxylic acid compound, the amide bond forming reaction can be controlled by utilizing a difference in reactivity between carboxyl groups.

Examples of the carboxylic acid compound include compounds represented by General Formula (A) below.

$$R^a\text{—COOH} \qquad \text{General Formula (A)}$$

Here, in the General Formula (A), $R^a$ represents an organic group.

A molecular weight of the carboxylic acid compound is not particularly limited and may be appropriately selected depending on the intended purpose. The molecular weight thereof is preferably 1,000 or less, more preferably 500 or less.

Specific examples of the carboxylic acid compound will be exemplified below. Needless to say, the carboxylic acid compound in the present invention is not limited to the following specific examples.

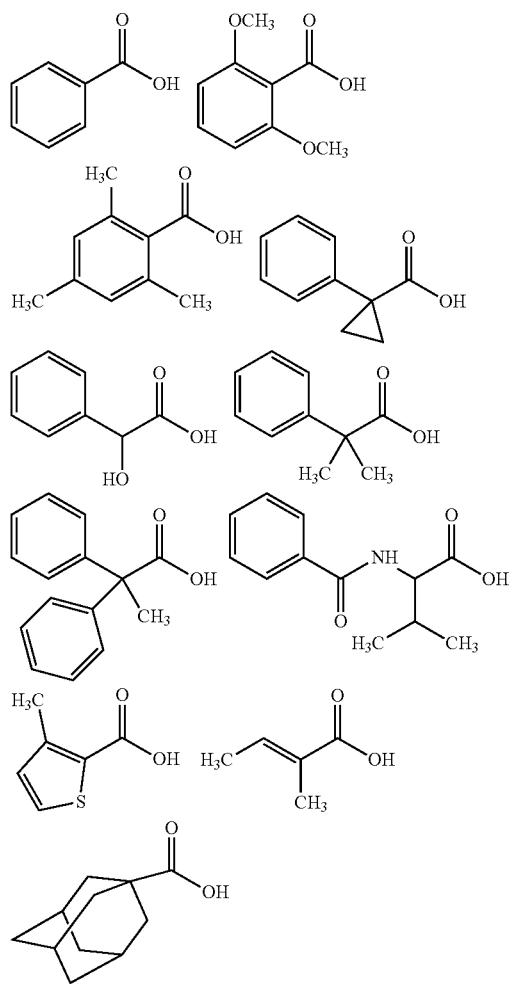

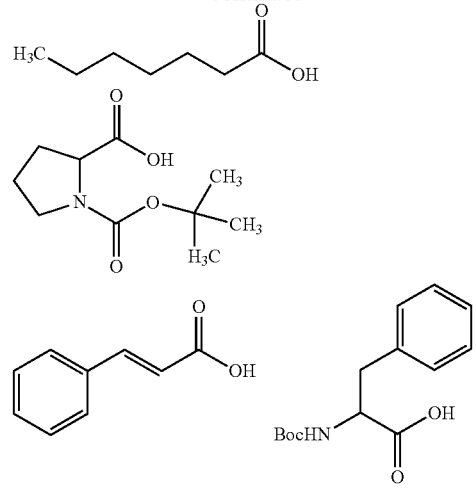

In the above Structural Formula, the "Boc" represents "t-butoxycarbonyl group".

Here, in the present invention, when a compound that includes an amino group including a protecting group (e.g., the above N-Boc phenylalanine) includes carboxylic acid, the compound belongs to the carboxylic acid compound.

Amine Compound

The amine compound is not particularly limited and may be appropriately selected depending on the intended purpose, so long as it is a compound having an amino group.

Examples of the amine compound include compounds represented by General Formula (B) below.

$$R^b\text{—}NR^cH \qquad \text{General Formula (B)}$$

Here, in the General Formula (B), $R^b$ represents an organic group, $R^c$ represents a hydrogen atom or an organic group, and $R^b$ and $R^c$ may be connected with each other to form a ring structure.

A molecular weight of the amine compound is not particularly limited and may be appropriately selected depending on the intended purpose. The molecular weight thereof is preferably 1,000 or less, more preferably 500 or less.

The amine compound may be a monoamine compound, or may be a polyamine compound. The amine compound is a compound having one amino group in a molecule thereof. The polyamine compound is a compound having two or more amino groups in a molecule thereof.

When the amine compound is the polyamine compound, the amide bond forming reaction can be controlled by utilizing a difference in reactivity between amino groups.

The amino group in the amine compound may be a primary amino group, or may be a secondary amino group.

Specific examples of the amine compound will be exemplified below. Needless to say, the amine compound in the present invention is not limited to the following specific examples.

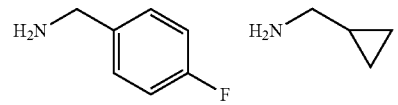

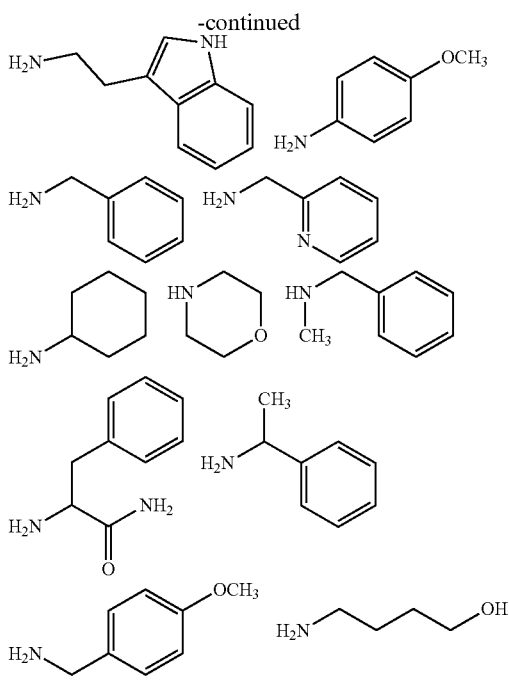

Amide Compound

The amide compound is not particularly limited and may be appropriately selected depending on the intended purpose, so long as it is a compound having an amide bond. Examples thereof include compounds represented by General Formula (C) below.

R$^a$—CONR$^c$—R$^b$      General Formula (C)

Here, in the General Formula (C), R$^a$ and R$^b$ each independently represent an organic group, and R$^c$ represents a hydrogen atom or an organic group, and R$^b$ and R$^c$ may be connected with each other to form a ring structure.

Reaction Conditions

Amount of Catalyst to be Used

In the method for forming the amide bond and the method for producing the amide compound, an amount of the catalyst to be used is not particularly limited and may be appropriately selected depending on the intended purpose. However, the catalyst of the present invention can allow reaction to proceed at a smaller amount than that of the conventional boron catalyst. In this point, the amount of the catalyst to be used is preferably 1 mol % to 10 mol %, more preferably 1 mol % to 8 mol %, particularly preferably 2 mol % to 7 mol %, relative to the amount of the substrate (e.g., the carboxylic acid compound).

Reaction Temperature and Reaction Time

A reaction temperature in each of the method for forming the amide bond and the method for producing the amide compound is not particularly limited and may be appropriately selected depending on the intended purpose. However, the catalyst of the present invention can allow reaction to proceed without requiring a high temperature (e.g., 150° C.).

In this point, the reaction temperature is preferably 30° C. to 120° C., more preferably 40° C. to 100° C.

The reaction time is not particularly limited and may be appropriately selected depending on the intended purpose. For example, the reaction time is 1 hour to 48 hours.

Other Conditions

A ratio between the carboxylic acid compound and the amine compound is not particularly limited and may be appropriately selected depending on the intended purpose. The ratio thereof is preferably carboxylic acid compound/amine compound=0.9 to 1.1 (molar ratio), more preferably an equivalent ratio, in terms of generation of less waste products.

The reaction in each of the method for forming the amide bond and the method for producing the amide compound is preferably performed in the presence of an organic solvent. Examples of the organic solvent include benzene, toluene, and xylene.

The reaction in each of the method for forming the amide bond and the method for producing the amide compound is preferably performed in an inert atmosphere. Examples of the inert atmosphere include a nitrogen atmosphere and an argon atmosphere.

EXAMPLES

The present invention will be described in detail with reference to the following Examples of the present invention. However, it should be noted that the present invention is not limited to these Examples.

Example 1

Synthesis of Compound (A-1)

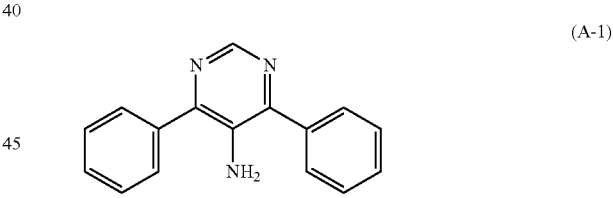

A reaction vessel was charged with 5-amino-4,6-dichloropyrimidine (1 eq, 5.0 g, 30.49 mmol), phenylboronic acid (2.2 eq, 8.2 g), tetrakis(triphenylphosphine)palladium(0) (0.02 eq, 0.70 g, 0.61 mmol), and potassium carbonate (4 eq, 16.9 g, 121.96 mmol), and was further charged with 1,4-dioxne•water mixture solution (5:1, 150 mL). The resultant was stirred at 80° C. in an argon atmosphere in a sealed tube for 16 hours. The resultant was cooled to room temperature, and distilled water (100 mL) and ethyl acetate (100 mL) were added thereto. The resultant was filtered through Celite and the filtrate was concentrated under reduced pressure. An organic layer and an aqueous layer were separated, and the aqueous layer was extracted twice with ethyl acetate (100 mL). All the organic layers were combined and were dehydrated by addition of anhydrous sodium sulfate, and the filtrate after the filtration was concentrated under reduced pressure. The resultant was recrystallized with ethanol to thereby obtain the above compound (A-1) as a grayish white solid with a yield of 90.1% (6.8 g, 27.50 mmol).

¹H NMR measurement results of the compound (A-1) obtained are as follows.

¹H NMR (400 MHz, Chloroform-d) δ 8.80 (s, 1H), 7.84-7.78 (m, 4H), 7.59-7.45 (m, 6H), 4.09 (s, 2H).

Synthesis of Compound (A-2)

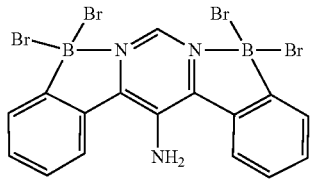

(A-2)

A reaction vessel that had been heated and dried was charged with the above compound (A-1) (1 eq, 4.0 g, 16.17 mmol), trimethylamine (2 eq, 4.5 mL, 32.35 mmol), and dichloromethane (32 mL). In an argon atmosphere, boron tribromide (1 M dichloromethane solution, 6 eq, 97 mL, 97.00 mmol) was added thereto and the resultant was stirred for 16 hours at room temperature. An aqueous potassium carbonate solution (50% w/v, 41.5 mL) was slowly added thereto and was stirred (the generated hydrobromic acid gas was disposed by passing it into a 2 N aqueous sodium hydroxide solution). The suspension containing an orange solid and a white solid was filtered. Then, tetrahydrofuran (100 mL) was added to the solid components and was stirred to selectively dissolve the orange solid. An insoluble component was filtered and separated, and the filtrate was concentrated under reduced pressure. Then, chloroform (25 mL) was added to the residue and was stirred for 10 minutes. The orange solid was filtered out and dried to thereby obtain the above compound (A-2) as an orange solid with a yield of 27.7% (2.63 g, 4.48 mmol).

¹H NMR measurement results of the compound (A-2) obtained are as follows.

¹H NMR (400 MHz, DMSO-d₆) δ 9.33 (s, 1H), 8.54 (d, J=8.2 Hz, 2H), 7.82 (dd, J=7.3, 1.4 Hz, 2H), 7.77 (td, J=7.3, 0.8 Hz, 2H), 7.65 (ddd, J=8.2, 7.3, 1.4 Hz, 2H), 7.43 (s, 2H).

Synthesis of Catalyst [Compound (A-3)]

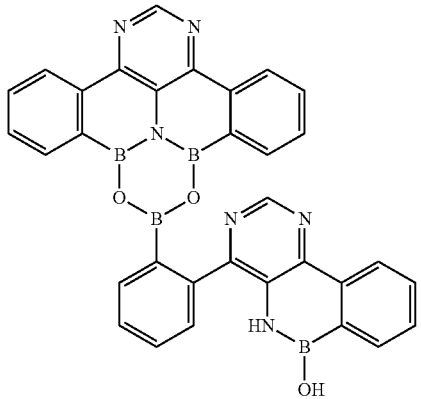

(A-3)

The above compound (A-2) (1 eq, 0.5 g, 0.85 mmol) was dissolved in tetrahydrofuran (8.5 mL) and an aqueous lithium hydroxide solution (2.45 M, 5 eq, 1.74 mL) was added thereto. Then, the resultant was stirred at room temperature for 0.5 hours. After an organic layer was separated, anhydrous sodium sulfate was added thereto for dehydration. The filtrate after the filtration was concentrated under reduced pressure. Ethyl acetate (5 mL) and water (5 mL) were added to the residue in this order and were stirred for 10 minutes to thereby obtain a suspension. A solid was filtered and was separated from the suspension to thereby obtain the above compound (A-3) as an orange solid with a yield of 72.9% (0.18 g, 0.31 mmol).

¹H NMR measurement results of the compound (A-3) obtained are as follows.

¹H NMR (400 MHz, DMSO-d₆) δ 9.35 (s, 1H), 9.23 (s, 1H), 8.95 (d, J=7.9 Hz, 2H), 8.89 (s, 2H), 8.90-8.83 (m, 2H), 8.53 (d, J=7.9 Hz, 1H), 8.36 (s, 1H), 8.29-8.22 (m, 1H), 8.03 (dd, J=7.6, 1.4 Hz, 2H), 7.89 (td, J=7.6, 1.7 Hz, 2H), 7.84 (ddd, J=8.5, 7.2, 1.4 Hz, 4H), 7.74 (dd, J=6.9, 1.4 Hz, 1H), 7.67 (td, J=7.5, 1.4 Hz, 2H), 7.67-7.57 (m, 4H).

Example 2

Synthesis of Catalyst [Compound (B-3)]

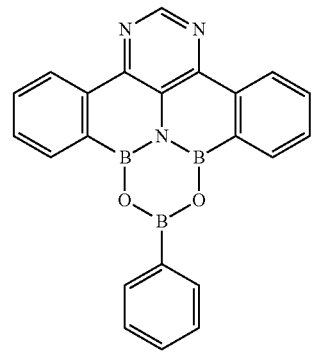

(B-3)

The above compound (A-2) (1 eq, 0.25 g, 0.43 mmol) and phenylboronic acid (5 eq, 0.26 g, 2.13 mmol) were dissolved in tetrahydrofuran (8.5 mL), and an aqueous lithium hydroxide solution (2.45 M, 5 eq, 1.74 mL) was added thereto. Then, the resultant was stirred at room temperature for 0.5 hours. After an organic layer was separated, anhydrous sodium sulfate was added thereto for dehydration. The filtrate after the filtration was concentrated under reduced pressure. Ethyl acetate (5 mL) was added to the residue and was stirred for 10 minutes to thereby obtain a suspension. A solid was filtered and separated from the suspension to thereby obtain the above compound (B-3) as an orange solid with a yield of 67.1% (0.11 g, 0.29 mmol).

¹H NMR measurement results of the compound (B-3) obtained are as follows.

¹H NMR (400 MHz, DMSO-d₆) δ 9.03 (s, 1H), 8.83 (d, J=7.9 Hz, 2H), 8.19 (d, J=7.9 Hz, 2H), 7.78-7.70 (m, 2H), 7.69-7.60 (m, 2H), 7.61-7.52 (m, 2H), 7.11-6.99 (m, 2H), 7.00-6.86 (m, 1H).

Example 3

Synthesis of Compound (C-1)

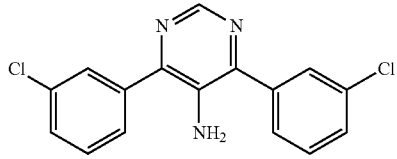

(C-1)

A reaction vessel was charged with 5-amino-4,6-dichloropyrimidine (1 eq, 0.95 g, 5.81 mmol), 3-chlorophenylboronic acid (2.2 eq, 2.0 g, 12.79 mmol), tetrakis(triphenylphosphine)palladium(0) (0.02 eq, 0.13 g, 0.12 mmol), and potassium carbonate (4 eq, 3.2 g, 23.25 mmol), and was further charged with a 1,4-dioxne•water mixture solution (5:1, 30 mL). The resultant was stirred at 80° C. in an argon atmosphere in a sealed tube for 16 hours. The resultant was cooled to room temperature, and distilled water (20 mL) and ethyl acetate (20 mL) were added thereto. The resultant was filtered through Celite and the filtrate was concentrated under reduced pressure. An organic layer and an aqueous layer were separated, and the aqueous layer was extracted twice with ethyl acetate (20 mL). All the organic layers were combined and were dehydrated by addition of anhydrous sodium sulfate, and the filtrate after the filtration was concentrated under reduced pressure. The resultant was recrystallized with ethanol to thereby obtain the above compound (C-1) as a grayish white solid with a yield of 56.0% (1.0 g, 3.26 mmol).

$^1$H NMR measurement results of the compound (C-1) obtained are as follows.

$^1$H NMR (400 MHz, Chloroform-d) δ 8.79 (s, 1H), 7.84-7.80 (m, 2H), 7.73-7.67 (m, 2H), 7.50-7.46 (m, 4H), 4.07 (s, 2H).

Synthesis of Compound (C-2)

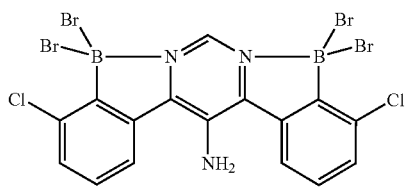

(C-2)

A reaction vessel that had been heated and dried was charged with the above compound (C-1) (1 eq, 0.5 g, 1.58 mmol), trimethylamine (2 eq, 0.44 mL, 3.16 mmol), and dichloromethane (3.2 mL). In an argon atmosphere, boron tribromide (1 M dichloromethane solution, 6 eq, 9.4 mL, 9.49 mmol) was added thereto and the resultant was stirred for 16 hours at room temperature. An aqueous potassium carbonate solution (50% w/v, 4.0 mL) was slowly added thereto and was stirred (the generated hydrobromic acid gas was disposed by passing it into a 2 N aqueous sodium hydroxide solution). The suspension containing an orange solid and a white solid was filtered. Then, tetrahydrofuran (15 mL) was added to the solid components and was stirred. The orange solid was selectively dissolved and filtered and the filtrate was concentrated under reduced pressure. Chloroform (5 mL) was added to the residue and the resultant was stirred for 10 minutes. Then, an insoluble component was filtered and separated. The filtrate was concentrated and dried under reduced pressure to thereby obtain the above compound (C-2) as an orange solid with a yield of 8.2% (0.086 g, 0.13 mmol).

$^1$H NMR measurement results of the compound (C-2) obtained are as follows.

$^1$H NMR (400 MHz, DMSO-$d_6$) δ 9.37 (s, 1H), 8.52 (d, J=7.9 Hz, 2H), 7.78 (d, J=7.9 Hz, 2H), 7.69 (t, J=7.9 Hz, 2H), 7.63 (s, 2H).

Synthesis of Catalyst [Compound (C-3)]

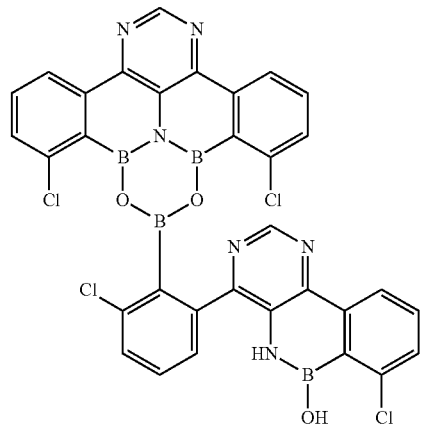

(C-3)

The above compound (C-2) (1 eq, 0.085 g, 0.13 mmol) was dissolved in tetrahydrofuran (1.3 mL), and an aqueous lithium hydroxide solution (2.45 M, 5 eq, 0.53 mL) was added thereto. Then, the resultant was stirred at room temperature for 0.5 hours. After an organic layer was separated, anhydrous sodium sulfate was added thereto for dehydration. The filtrate after the filtration was concentrated under reduced pressure. Ethyl acetate (5 mL) and water (5 mL) were added to the residue in this order and were stirred for 10 minutes to thereby obtain a suspension. A solid was filtered and was separated from the suspension to thereby obtain the above compound (C-3) as an orange solid with a yield of 21.4% (0.020 g, 0.028 mmol).

$^1$H NMR measurement results of the compound (C-3) obtained are as follows.

$^1$H NMR (400 MHz, DMSO-$d_6$) δ 9.53 (s, 1H), 9.22 (s, 1H), 8.99 (s, 1H), 8.98 (d, J=1.1 Hz, 1H), 8.96 (d, J=1.1 Hz, 1H), 8.93 (dd, J=5.7, 3.5 Hz, 1H), 8.48 (d, J=7.6 Hz, 1H), 8.31 (s, 1H), 7.86 (s, 1H), 7.84 (d, J=2.4 Hz, 1H), 7.81-7.76 (m, 2H), 7.69 (t, J=7.8 Hz, 1H), 7.66-7.60 (m, 3H).

Example 4

Synthesis of N-(4-fluorobenzyl)-2-methyl-2-phenylpropanamide

The catalyst (A-3) obtained in Example 1 was used to synthesize N-(4-fluorobenzyl)-2-methyl-2-phenylpropanamide.

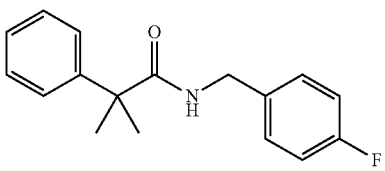 [SMILES: CC(C)(C(=O)NCc1ccc(F)cc1)c1ccccc1]

A reaction vessel was charged with 2-methyl-2-phenyl-propanoic acid (1 eq, 49.3 mg, 0.30 mmol), the catalyst (A-3) (0.05 eq, 8.7 mg, 0.015 mmol), and fluorobenzene (5 mL) in this order to thereby obtain a suspension. Then, 4-fluorobenzylamine (1 eq, 34.3 μL, 0.30 mmol) was added thereto at room temperature, and was stirred for 8 hours in an argon atmosphere under the heating and refluxing condition (the cooled water-azeotrope was passed through a pellet (8 to 12 mesh) molecular sieve layer (1.8 g) and then was refluxed to the reaction solution). Ethyl acetate (5 mL) was added to the residue obtained by concentrating the reaction solution under reduced pressure, and an insoluble component was filtered and separated. The filtrate after the filtration was concentrated under reduced pressure. When $^1$H-NMR of the reaction mixture was analyzed, the above compound was obtained with a yield of more than 95%.

Comparative Example 1

As a catalyst, 2,4,6-triphenylboroxin was used to attempt synthesis of N-(4-fluorobenzyl)-2-methyl-2-phenylpropanamide.

To a reaction vessel that had been charged with molecular sieve 4A (67 mg) and had been dried by application of heat under reduced pressure, 2-methyl-2-phenylpropanoic acid (13.4 mg, 81.6 μmol) and 2,4,6-triphenylboroxin (1.3 mg, 4.16 μmol) were added to form a toluene (820 μL) solution. After 4-fluorobenzylamine (9.28 μL, 81.6 μmol) was added thereto at room temperature and the resultant was stirred at 80° C. for 18 hours in an argon atmosphere, the reaction liquid was cooled to room temperature. Distilled water (0.5 mL) was added to the reaction liquid, followed by stirring. The separated aqueous layer was extracted four times with ethyl acetate (1.5 mL). Then, all the organic layers were combined and a saturated aqueous solution of sodium chloride (1.5 mL) was added thereto. The resultant was stirred and was washed. To the organic layer that had been separated again, anhydrous sodium sulfate was added for dehydration. Then, the filtrate after the filtration was concentrated under reduced pressure. When the reaction mixture was analyzed through $^1$H-NMR, generation of N-(4-fluorobenzyl)-2-methyl-2-phenylpropanamide was not found.

Example 5

Synthesis of Compound Below

The catalyst (A-3) obtained in Example 1 was used to synthesize the following compound.

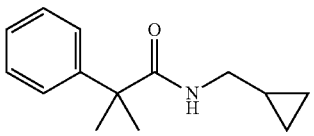 [SMILES: CC(C)(C(=O)NCC1CC1)c1ccccc1]

A reaction vessel was charged with 2-methyl-2-phenyl-propanoic acid (1 eq, 49.3 mg, 0.30 mmol), the catalyst (A-3) (0.05 eq, 8.7 mg, 0.015 mmol), and fluorobenzene (5 mL) in this order to thereby obtain a suspension. Cyclopropylmethylamine (1 eq, 25.9 μL, 0.30 mmol) was added thereto at room temperature, and was stirred for 8 hours in an argon atmosphere under the heating and refluxing condition (the cooled water-azeotrope was passed through a pellet (8 to 12 mesh) molecular sieve layer (1.8 g) and then was refluxed to the reaction solution). Ethyl acetate (5 mL) was added to the residue obtained by concentrating the reaction solution under reduced pressure, and an insoluble component was filtered and separated. The filtrate after the filtration was concentrated under reduced pressure. When 1H-NMR of the reaction mixture was analyzed, the above compound was obtained with a yield of 69%.

Example 6

Synthesis of Compound Below

The catalyst (A-3) obtained in Example 1 was used to synthesize the following compound.

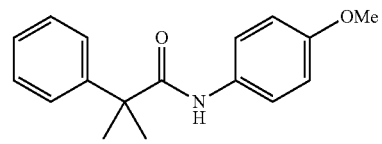 [SMILES: COc1ccc(NC(=O)C(C)(C)c2ccccc2)cc1]

A reaction vessel was charged with 2-methyl-2-phenyl-propanoic acid (1 eq, 49.3 mg, 0.30 mmol), the catalyst (A-3) (0.05 eq, 8.7 mg, 0.015 mmol), and fluorobenzene (5 mL) in this order to thereby obtain a suspension. p-Anisidine (1 eq, 36.9 mg, 0.30 mmol) was added thereto at room temperature, and was stirred for 14 hours in an argon atmosphere under the heating and refluxing condition (the cooled water-azeotrope was passed through a pellet (8 to 12 mesh) molecular sieve layer (1.8 g) and then was refluxed to the reaction solution). Ethyl acetate (5 mL) was added to the residue obtained by concentrating the reaction solution under reduced pressure, and an insoluble component was filtered and separated. The filtrate after the filtration was concentrated under reduced pressure. When $^1$H-NMR of the reaction mixture was analyzed, the above compound was obtained with a yield of 47%.

Example 7

Synthesis of Compound Below

The catalyst (A-3) obtained in Example 1 was used to synthesize the following compound.

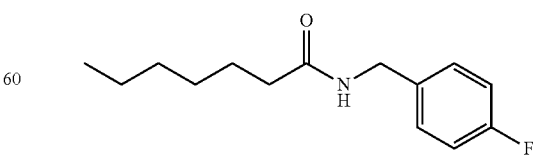

A reaction vessel was charged with heptanoic acid (1 eq, 12.7 μL, 0.10 mmol), the catalyst (A-3) (0.05 eq, 2.9 mg, 0.005 mmol), and fluorobenzene (5 mL) in this order to thereby obtain a suspension. Then, 4-fluorobenzylamine (1 eq, 11.4 μL, 0.10 mmol) was added thereto at room temperature and was stirred for 4 hours in an argon atmosphere under the heating and refluxing condition (the cooled water-azeotrope was passed through a pellet (8 to 12 mesh) molecular sieve layer (0.6 g) and then was refluxed to the reaction solution). Ethyl acetate (5 mL) was added to the residue obtained by concentrating the reaction solution under reduced pressure, and an insoluble component was filtered and separated. The filtrate after the filtration was concentrated under reduced pressure. When ¹H-NMR of the reaction mixture was analyzed, the above compound was obtained with a yield of more than 95%.

Example 8

Synthesis of Compound Below

The catalyst (A-3) obtained in Example 1 was used to synthesize the following compound.

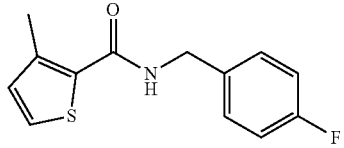 [SMILES: Cc1ccsc1C(=O)NCc1ccc(F)cc1]

A reaction vessel was charged with 3-methyl-2-thiophencarboxylic acid (1 eq, 42.7 mg, 0.30 mmol), the catalyst (A-3) (0.05 eq, 8.7 mg, 0.015 mmol), and fluorobenzene (5 mL) in this order to thereby obtain a suspension. 4-Fluorobenzylamine (1 eq, 34.3 μL, 0.30 mmol) was added thereto at room temperature, and was stirred for 14 hours in an argon atmosphere under the heating and refluxing condition (the cooled water-azeotrope was passed through a pellet (8 to 12 mesh) molecular sieve layer (1.8 g) and then was refluxed to the reaction solution). Ethyl acetate (5 mL) was added to the residue obtained by concentrating the reaction solution under reduced pressure, and an insoluble component was filtered and separated. The filtrate after the filtration was concentrated under reduced pressure. When ¹H-NMR of the reaction mixture was analyzed, the above compound was obtained with a yield of 66%.

Example 9

Synthesis of Compound Below

The catalyst (A-3) obtained in Example 1 was used to synthesize the following compound.

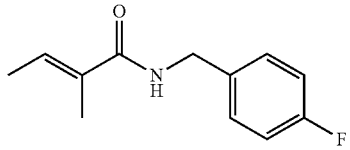

A reaction vessel was charged with tiglic acid (1 eq, 30.3 μL, 0.30 mmol), the catalyst (A-3) (0.05 eq, 8.7 mg, 0.015 mmol), and fluorobenzene (5 mL) in this order to thereby obtain a suspension. 4-Fluorobenzylamine (1 eq, 34.3 μL, 0.30 mmol) was added thereto at room temperature, and was stirred for 14 hours in an argon atmosphere under the heating and refluxing condition (the cooled water-azeotrope was passed through a pellet (8 to 12 mesh) molecular sieve layer (1.8 g) and then was refluxed to the reaction solution). Ethyl acetate (5 mL) was added to the residue obtained by concentrating the reaction solution under reduced pressure, and an insoluble component was filtered and separated. The filtrate after the filtration was concentrated under reduced pressure. When ¹H-NMR of the reaction mixture was analyzed, the above compound was obtained with a yield of more than 95%.

Example 10

Synthesis of Compound Below

The catalyst (A-3) obtained in Example 1 was used to synthesize the following compound.

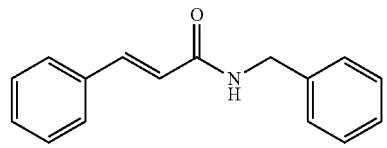 [SMILES: O=C(/C=C/c1ccccc1)NCc1ccccc1]

A reaction vessel was charged with cinnamic acid (1 eq, 44.4 mg, 0.30 mmol), the catalyst (compound A-3) (0.05 eq, 8.7 mg, 0.015 mmol), and fluorobenzene (5 mL) in this order to thereby obtain a suspension. Benzylamine (1 eq, 32.8 μL, 0.30 mmol) was added thereto at room temperature, and was stirred for 16 hours in an argon atmosphere under the heating and refluxing condition (the cooled water-azeotrope was passed through a pellet (8 to 12 mesh) molecular sieve layer (1.8 g) and then was refluxed to the reaction solution). Ethyl acetate (5 mL) was added to the residue obtained by concentrating the reaction solution under reduced pressure, and an insoluble component was filtered and separated. The filtrate after the filtration was concentrated under reduced pressure. When ¹H-NMR of the reaction mixture was analyzed, the above compound was obtained with a yield of more than 95%.

Example 11

Synthesis of Compound Below

The catalyst (A-3) obtained in Example 1 was used to synthesize the following compound.

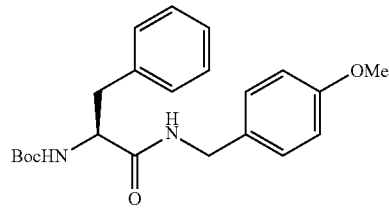 [SMILES: COc1ccc(CNC(=O)[C@H](Cc2ccccc2)NC(=O)OC(C)(C)C)cc1]

A reaction vessel was charged with N-Boc phenylalanine (1 eq, 79.6 mg, 0.30 mmol), the catalyst (A-3) (0.05 eq, 8.7 mg, 0.015 mmol), and fluorobenzene (5 mL) in this order to thereby obtain a suspension. 4-Methoxybenzylamine (1 eq, 30.5 μL, 0.30 mmol) was added thereto at room temperature, and was stirred for 8 hours in an argon atmosphere under the heating and refluxing condition (the cooled water-azeotrope was passed through a pellet (8 to 12 mesh) molecular sieve layer (1.8 g) and then was refluxed to the reaction solution). Ethyl acetate (5 mL) was added to the residue obtained by concentrating the reaction solution under reduced pressure, and an insoluble component was filtered and separated. The filtrate after the filtration was concentrated under reduced pressure. When $^1$H-NMR of the reaction mixture was analyzed, the above compound was obtained with a yield of more than 95%.

Note that, the "Boc" described above represents "t-butoxycarbonyl group".

Example 12

Synthesis of Compound Below

The catalyst (A-3) obtained in Example 1 was used to synthesize the following compound.

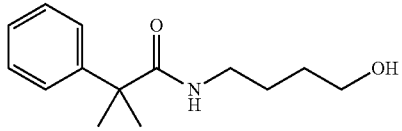 [SMILES: CC(C)(C(=O)NCCCCO)c1ccccc1]

A reaction vessel was charged with 2-methyl-2-phenyl-propanoic acid (1 eq, 49.3 mg, 0.30 mmol), the catalyst (0.05 eq, 8.7 mg, 0.015 mmol), and fluorobenzene (5 mL) in this order to thereby obtain a suspension. 4-Amino-1-butanol (1 eq, 27.7 μL, 0.30 mmol) was added thereto at room temperature, and was stirred for 16 hours in an argon atmosphere under the heating and refluxing condition (the cooled water-azeotrope was passed through a pellet (8 to 12 mesh) molecular sieve layer (1.8 g) and then was refluxed to the reaction solution). Ethyl acetate (5 mL) was added to the residue obtained by concentrating the reaction solution under reduced pressure, and an insoluble component was filtered and separated. The filtrate after the filtration was concentrated under reduced pressure. When $^1$H-NMR of the reaction mixture was analyzed, the above compound was obtained with a yield of 93%.

Example 13

Synthesis of Compound Below

The catalyst (B-3) obtained in Example 2 was used to synthesize the following compound.

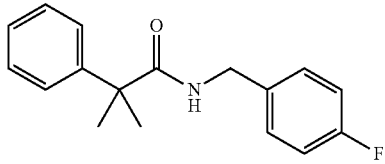 [SMILES: CC(C)(C(=O)NCc1ccc(F)cc1)c1ccccc1]

A reaction vessel was charged with 2-methyl-2-phenyl-propanoic acid (1 eq, 49.3 mg, 0.30 mmol), the catalyst (B-3) (0.05 eq, 5.8 mg, 0.015 mmol), and fluorobenzene (5 mL) in this order to thereby obtain a suspension. 4-Fluorobenzylamine (1 eq, 34.3 μL, 0.30 mmol) was added thereto at room temperature, and was stirred for 8 hours in an argon atmosphere under the heating and refluxing condition (the cooled water-azeotrope was passed through a pellet (8 to 12 mesh) molecular sieve layer (1.8 g) and then was refluxed to the reaction solution). Ethyl acetate (5 mL) was added to the residue obtained by concentrating the reaction solution under reduced pressure, and an insoluble component was filtered and separated. The filtrate after the filtration was concentrated under reduced pressure. When $^1$H-NMR of the reaction mixture was analyzed, the above compound was obtained with a yield of 32%.

Example 14

Synthesis of Compound Below

The catalyst (C-3) obtained in Example 3 was used to synthesize the following compound.

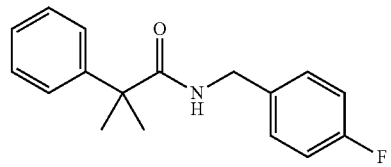 [SMILES: CC(C)(C(=O)NCc1ccc(F)cc1)c1ccccc1]

A reaction vessel was charged with 2-methyl-2-phenyl-propanoic acid (1 eq, 49.3 mg, 0.30 mmol), the catalyst (C-3) (0.05 eq, 10.7 mg, 0.015 mmol), and fluorobenzene (5 mL) in this order to thereby obtain a suspension. 4-Fluorobenzylamine (1 eq, 34.3 μL, 0.30 mmol) was added thereto at room temperature, and was stirred for 8 hours in an argon atmosphere under the heating and refluxing condition (the cooled water-azeotrope was passed through a pellet (8 to 12 mesh) molecular sieve layer (1.8 g) and then was refluxed to the reaction solution). Ethyl acetate (5 mL) was added to the residue obtained by concentrating the reaction solution under reduced pressure, and an insoluble component was filtered and separated. The filtrate after the filtration was concentrated under reduced pressure. When $^1$H-NMR of the reaction mixture was analyzed, the above compound was obtained with a yield of 25%.

Example 15

Collection and Reutilization Experiment

The catalyst (A-3) obtained in Example 1 was used to synthesize the following compound. The following compound was synthesized several times, while the catalyst (A-3) was collected and reutilized.

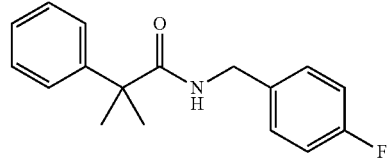 [SMILES: CC(C)(C(=O)NCc1ccc(F)cc1)c1ccccc1]

A reaction vessel was charged with 2-methyl-2-phenyl-propanoic acid (1 eq, 49.3 mg, 0.30 mmol), the catalyst (A-3) (0.05 eq, 8.7 mg, 0.015 mmol), and fluorobenzene (5 mL) in this order to thereby obtain a suspension. 4-Fluorobenzylamine (1 eq, 34.3 μL, 0.30 mmol) was added thereto at room temperature, and was stirred for 8 hours in an argon atmosphere under the heating and refluxing condition (the cooled water-azeotrope was passed through a pellet (8 to 12 mesh) molecular sieve layer (1.8 g) and then was refluxed to the reaction solution). Ethyl acetate (5 mL) was added to the residue obtained by concentrating the reaction solution under reduced pressure, and an insoluble component was filtered and separated. The filtrate after the filtration was concentrated under reduced pressure. When $^1$H-NMR of the reaction mixture was analyzed, the above compound was obtained with a yield of more than 95%.

The insoluble component that had been filtered and separated was used as a catalyst (4.6 mg, 0.008 mmol), 2-methyl-2-phenylpropanoic acid (1 eq, 26.3 mg, 0.16 mmol), fluorobenzene (5 mL), and 4-fluorobenzylamine (1 eq, 18.3 μL, 0.30 mmol) were added thereto in this order. Then, the resultant was stirred for 8 hours in an argon atmosphere under the heating and refluxing condition (the cooled water-azeotrope was passed through a pellet (8 to 12 mesh) molecular sieve layer (0.94 g) and then was refluxed to the reaction solution). Ethyl acetate (5 mL) was added to the residue obtained by concentrating the reaction solution under reduced pressure, and an insoluble component was filtered and separated. The filtrate after the filtration was concentrated under reduced pressure. When $^1$H-NMR of the reaction mixture was analyzed, the above compound was obtained with a yield of 85%.

The insoluble component that had been further filtered and separated was used as a catalyst (1.4 mg, 0.0024 mmol), and 2-methyl-2-phenylpropanoic acid (1 eq, 7.9 mg, 0.048 mmol), fluorobenzene (5 mL), and 4-fluorobenzylamine (1 eq, 5.5 μL, 0.30 mmol) were also added thereto in this order. Then, the resultant was stirred for 8 hours in an argon atmosphere under the heating and refluxing condition (the cooled water-azeotrope was passed through a pellet (8 to 12 mesh) molecular sieve layer (0.94 g) and then was refluxed to the reaction solution). Ethyl acetate (5 mL) was added to the residue obtained by concentrating the reaction solution under reduced pressure, and an insoluble component was filtered and separated. The filtrate after the filtration was concentrated under reduced pressure. When $^1$H-NMR of the reaction mixture was analyzed, the above compound was obtained with a yield of more than 95%.

From the result of the aforementioned Example 15, it was confirmed that the catalyst of the present invention can be easily collected and reutilized. The reason for this is because the catalyst of the present invention has a considerably low solubility in a solvent and maintains its structure even after reaction. It is assumed that inclusion of a pyrimidine ring in the catalyst of the present invention effectively contributes to the aforementioned effect.

Meanwhile, the following catalyst, which has been reported by the present inventors in Non-Patent Literature [Nature Chemistry 9, 571-577 (2017)], has solubility in a solvent. Therefore, it was difficult to collect the catalyst after amidation reaction, and the catalyst could not be collected and reutilized.

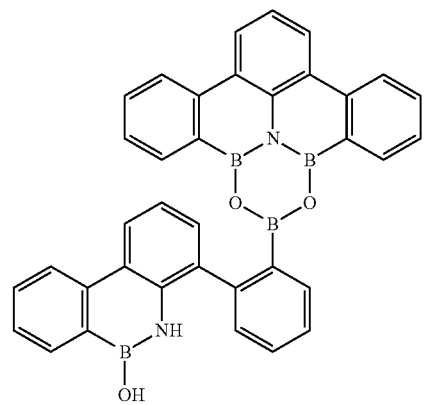

From the above results, it could be confirmed that the catalyst of the present invention could be used for reaction for synthesizing an amide compound from various carboxylic acid compounds and various amine compounds. Particularly, one of the most excellent advantages of the catalyst of the present invention is that amide bond forming reaction can be performed even when sterically bulky carboxylic acid compounds such as N-Boc phenylalanine are used, which is not observed in amide bond forming reaction using conventional boron catalysts.

The catalyst of the present invention did not use an expensive modified boron reagent and can be produced with less steps, compared to the catalyst that had been reported in Non-Patent Literature [Nature Chemistry 9, 571-577 (2017)].

Moreover, the catalyst of the present invention could be collected and reutilized compared to the catalyst that had been reported in Non-Patent Literature [Nature Chemistry 9, 571-577 (2017)].

INDUSTRIAL APPLICABILITY

The catalyst of the present invention can suitably be used for amide bond forming reaction.

Aspects of the present invention are as follows, for example.

<1> A catalyst represented by General Formula (1) below:

General Formula (1)

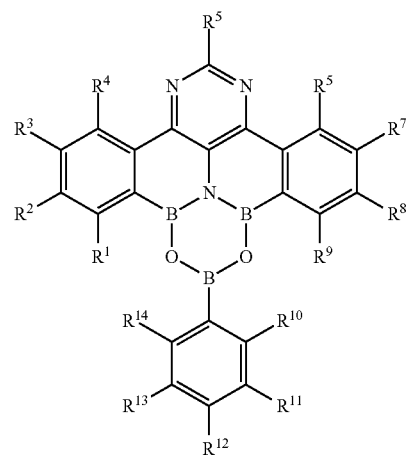

where in the General Formula (1), $R^1$ to $R^{14}$ each independently represent a hydrogen atom or a substituent.

<2> The catalyst according to <1>, wherein the substituent is an electron donative group or an electron attractive group.

<3> The catalyst according to <1> or <2>, wherein the catalyst is represented by General Formula (1A) below or General Formula (1B) below:

General Formula (1A)

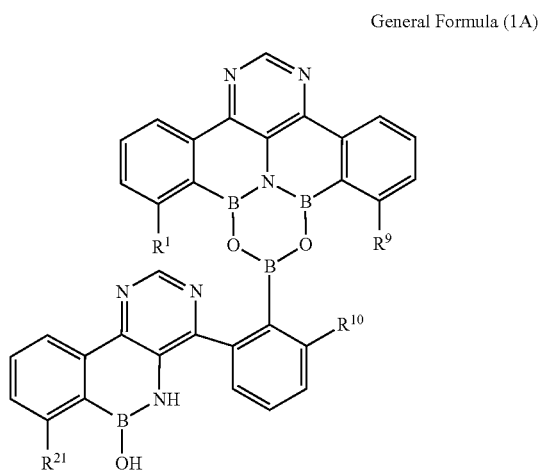

General Formula (1B)

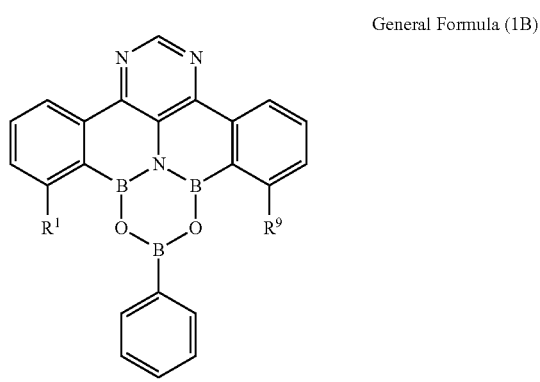

where in the General Formula (1A), $R^1$, $R^9$, $R^{10}$, and $R^{21}$ each independently represent a hydrogen atom, an electron donative group, or an electron attractive group, and where in the General Formula (1B), $R^1$ and $R^9$ each independently represent a hydrogen atom, an electron donative group, or an electron attractive group.

<4> A method for forming an amide bond, the method including:

reacting a carboxyl group of a carboxylic acid compound with an amino group of an amine compound in the presence of the catalyst according to any one of <1> to <3> to form the amide bond.

<5> A method for producing an amide compound, the method including:

reacting a carboxylic acid compound with an amine compound in the presence of the catalyst according to any one of <1> to <3> to obtain the amide compound.

The invention claimed is:

1. A catalyst represented by General Formula (1) below:

General Formula (1)

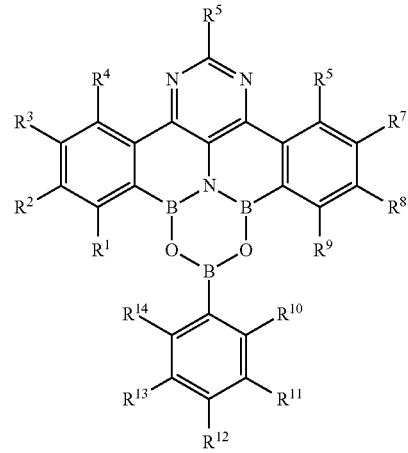

where in the General Formula (1), $R^1$ to $R^{14}$ each independently represent a hydrogen atom, an electron donative group or an electron attractive group.

2. The catalyst according to claim 1,

Wherein $R^{10}$ and $R^{14}$ are each independently represented by General Formula (2) below as the electron attractive group, or General Formula (3) below as the electron attractive group:

General Formula (2)

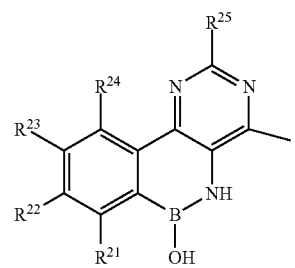

wherein in the General Formula (2), $R^{21}$ to $R^{25}$ each independently represent a hydrogen atom, an electron donative group or an electron attractive group;

General Formula (3)

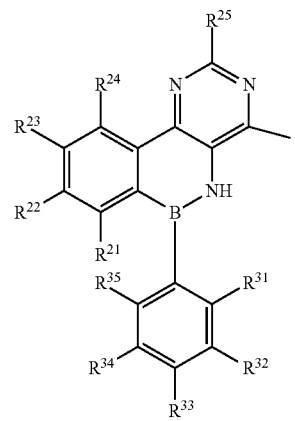

wherein in the General Formula (3), $R^{21}$ to $R^{25}$ and $R^{31}$ to $R^{35}$ each independently represent a hydrogen atom, an electron donative group or an electron attractive group.

3. The catalyst according to claim 1, wherein the catalyst is represented by General Formula (1A) below or General Formula (1B) below:

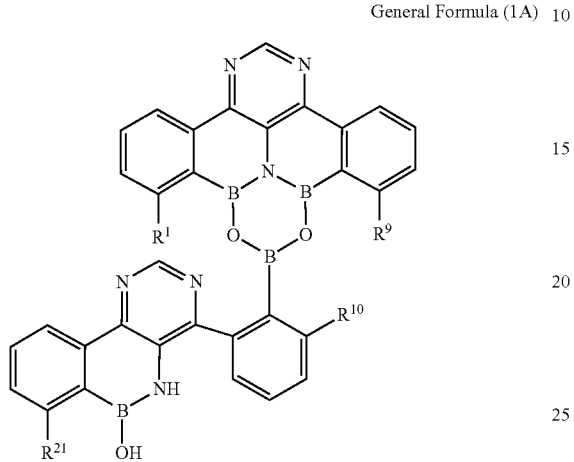

General Formula (1A)

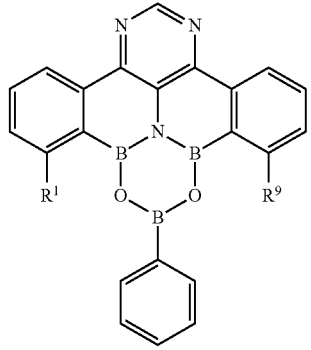

General Formula (1B)

where in the General Formula (1A), $R^1$, $R^9$, $R^{10}$, and $R^{21}$ each independently represent a hydrogen atom, an electron donative group, or an electron attractive group, and where in the General Formula (1B), $R^1$ and $R^9$ each independently represent a hydrogen atom, an electron donative group, or an electron attractive group.

4. A method for producing an amide compound, the method comprising:

reacting a carboxylic acid compound with an amine compound in the presence of the catalyst according to claim 1 to obtain the amide compound.

* * * * *